United States Patent [19]

Popoff et al.

[11] 4,220,589

[45] Sep. 2, 1980

[54] N-(OXAZOLIDINOTHIO) IMIDES THAT PROVIDE SCORCH RETARDANT NONBLOOMING ELASTOMERIC COMPOSITIONS

[75] Inventors: Ivan C. Popoff, Upper Dublin Township, Montgomery County; Everett A. Mailey, Plymouth Township, Montgomery County; Paul G. Haines, Lafayette Hill, all of Pa.

[73] Assignee: Pennwalt Corporation, Philadelphia, Pa.

[21] Appl. No.: 909,596

[22] Filed: May 23, 1978

[51] Int. Cl.$^2$ ............................................. C07D 263/32
[52] U.S. Cl. .................................. 548/215; 260/784; 525/348
[58] Field of Search ..................... 260/307 C, 307 FA

[56] References Cited

U.S. PATENT DOCUMENTS

| 3,838,114 | 9/1974 | Lawrence | 260/79.5 A |
| 3,928,340 | 12/1975 | Lawrence | 260/247.1 L |

*Primary Examiner*—Jose Tovar
*Attorney, Agent, or Firm*—David Edwards

[57] ABSTRACT

A selected group of N-(oxazolidinothio) imides are active as scorch retarders without causing bloom in both unsaturated elastomers and elastomers with a slight degree of unsaturation.

7 Claims, No Drawings

N-(OXAZOLIDINOTHIO) IMIDES THAT PROVIDE SCORCH RETARDANT NONBLOOMING ELASTOMERIC COMPOSITIONS

BACKGROUND OF THE INVENTION

This invention relates to a selected group of N-(oxazolidinothio)imides active as scorch retarders both in unsaturated elastomers (e.g. SBR, natural, rubber, Neoprene) and in elastomers with a very low degree of unsaturation (e.g. EPDM). They are active with ultra accelerators, do not cause blooming, are thermally stable, and are not detrimental to the aging properties of the vulcanizates. The selection of these compounds is highly specific and is limited by the nature of both the cyclic amine moiety and the imide.

Blooming is objectionable in rubber items for a variety of reasons, such as:

(a) technical [adhesion of rubber layers to each other or to other substrates is weakened or even prevented (for the effect of bloom on tack see O.K.F. Busenmaker, Rubber Chemistry and Technology, 37, 1178 (1964); J. A. Schaldeman, "Novel Theory for the Action of Phenolic Tackifiers" Paper No. 13, Rubber Div. of A.C.S., 112th Meeting of Oct. 1977); defects in the function of electrical parts insulated with rubber or made of rubber];

(b) health [possible skin irritation and/or sensitization];

(c) economic [off-spec items; lower quality items]; and (d) aesthetic [surface of rubber item is dull or dusty, or oily, slippery or sticky].

Considerable concern over blooming exists in the art. For example, see U.S. Pat. No. 3,780,001.

The very limited class and highly selective retarders of this invention do not cause blooming in non-blooming rubber acceleration systems, contrary to N-(alkylthio)imides, such as N-(cyclohexylthio)phthalimide that is a widely used retarder (see U.S. Pat. No. 3,546,185); N-(aminothio)imides outside of this class, such as N-(morpholinothio)phthalimide, N-(piperidinothio)phthalimide, and N-[(N',N'-benzylethylamino)thio]phthalimide produce blooming in such systems. These blooming imides are described in U.S. Pat. Nos. 3,838,114 and 3,928,340. Certain oxazolidinothioamides, such as N-phenyl-N-[(2-trichloromethyloxazolidino)thio]benzamide and N,N'Bis[(2-trichloromethyloxazolidino)thio]oxanilide, described in this application for comparison purposes and related to known aminothioamides such as are disclosed in U.S. Pat. No. 3,910,864, likewise are undesirable because of excessive blooming.

Thus the non-blooming characteristics and, as shown later, even the scorch retarding activity of the oxazolidinothioimides are not predictable within their class of compounds and are limited to a relatively small selection of structures. The new retarders do not cause blooming even when used at levels higher than necessary. Such excess use of retarder can be highly advantageous as the retardation effect is increased which can overcome or prevent poor results from imprecision such as weighing errors with respect to non-blooming rubber processing ingredients.

Additional examples illustrative of lack of predictability in blooming (and in scorch retardation) are: (a) according to U.S. Pat. No. 3,780,001, the retarder N,N'-bis(cyclohexylthio)oxanilide blooms less while Santoguard PVI, i.e. N-(cyclohexylthio)phthalimide, (hereinafter "PVI"), causes more bloom at higher than at lower levels; (b) the oxalamide N,N'-bis(cyclohexylthio)oxamide does not bloom in EPDM but its diphenyl-derivative N,N'-bis(cyclohexylthio)oxanilide causes blooming both in EPDM and in natural rubber at the practical level of 0.5 phr. (parts per 100 parts elastomer or rubber); (c) some oxazolidino-derivatives of amides and imides, including oxalamides either bloom or do not have any significant scorch retarding activity as shown in Tables 1 and 2, infrar for N-[spiro(cyclohexane-1,2'-oxazolidino)thio]phthalimide, N-[spiro(cyclohexane-1,2'-oxazolidino)thio]succinimide, N-phenyl-N-[(2-trichloromethyloxazolidino)thio]benzamide, N,N'bis[(2-trichloromethyloxazolidino)thio]oxanilide, N-butyl-N[(2-trichloromethyloxazolidino)thio]acetamide, N-[(2-trichloromethyloxazolidino)thio]diacetimide and N,N-bis[(2-trichloromethyloxazolidino)thio]acetamide.

SUMMARY OF THE INVENTION

The improved composition of this invention is defined as in a sulfur vulcanizable elastomeric polymer composition comprising an admixture of a sulfur vulcanizable elastomeric polymer, sulfur, and other rubber compounding ingredients, the improvement which comprises incorporation within the admixture of a scorch-retardant effective amount of at least one N-(oxazolidinothio)imide compound having the structural formula:

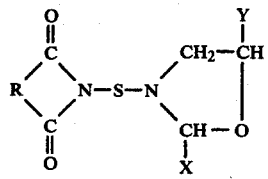

wherein R is an organic divalent radical selected from the group consisting of ortho-phenylene, 1,2-cyclohex-4-enediyl, 1,2-cyclohexanediyl, 4-methyl-1,2-cyclohexanediyl, 1,2-ethanediyl, and 1,2-ethenediyl; furthermore R can be the divalent radical:

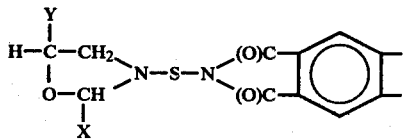

X is a monovalent organic radical selected from the group consisting of phenyl and trichloromethyl radicals; Y is hydrogen with the proviso that Y can be phenyl when X is trichloromethyl; to provide a polymer composition having a high scorch resistance, and final curved vulcanized articles that are bloom resistant.

Preferred imides are: N-[(2-trichloromethyloxazolidino)thio]phthalimide, N-[(5-phenyl-2-trichloromethyloxazolidino)thio]phthalimide, N-[(5-phenyl-2-trichloromethyloxazolidino)thio]succinimide, N-[(2-trichloromethyloxazolidino)thio]succinimide, N-[(2-Trichloromethyloxazolidino)thio]maleimide and N-[(2-phenyloxazolidino)thio]phthalimide.

The improved method of this invention is defined as an improvement in the method of curing a sulfur vulcanizable elastomeric polymer composition comprising an admixture of a sulfur vulcanizable elastomeric polymer, sulfur and other rubber compounding ingredients, the improvement which comprises incorporating within the admixture a scorch retardant effective amount of at least one N-(oxazolidinothio) imide compound having the above structural formula, and further providing a polymer composition having a high scorch resistance, and final vulcanized articles that are bloom resistant.

The preferred imides of the invention and for the practice of the method are the same as above with respect to the composition of the invention.

DESCRIPTION OF THE PREFERRED EMBODIMENTS

The preparation of the non-blooming retarders of this invention are described in Examples 1-6. Preparation of comparative compounds are shown in Examples 7-21. The elastomer compounding (Recipes 1-3) for testing and evaluation are also shown.

The ingredients of each recipe are mixed on a 2-roll laboratory rubber mill and cured in a conventional manner. The bloom observations are made at least one week after curing.

The scorch (minutes for 3-point rise over the minimum viscosity) is measured with Monsanto's Mooney Viscometer that is widely used in the trade. The results of Tables 1 and 2 are reported in terms of percentages relative to the control in which no retarder is used. This recording method allows a direct and reliable comparison of all chemical compositions. Unless the scorch value is higher than 110% of the control, it was not considered indicative of scorch retardation activity. A value of less than 100% of the control indicates that the respective retarder candidate aggravates the scorchiness.

U.S. Pat. No. 3,838,114 discloses 5-membered N-O-rings (oxazolidines) as the amine moiety but the "divisional" of this patent (U.S. Pat. No. 3,928,340) does not include any amine moieties with 5-membered amine structure and its only N-O-ring is 6-membered ring i.e. a morpholine. The only 5-membered cyclic amine moiety mentioned in U.S. Pat. No. 3,838,114 (line 37 of column 3) is pyrrolidine; EPDM and Neoprene are not one of the many elastomers (column 9) used in the tests. The author of these two patents discloses in his publication in *Rubber Chemistry and Technology*, 49, p. 334 and 399 (compound 2) that the pyrrolidinothioimide mentioned in U.S. Pat. No. 3,838,114 "decomposed before could be tested"; thus it was not tested although line 69 of Column 8 of U.S. Pat. No. 3,838,114 mentions, apparently in error, that "all of the compounds either performed as an activator or a retarder".

EXAMPLE 1

N-[(2-Trichloromethyloxazolidino)thio]phthalimide

A solution of 12.0 g (0.070 mole) of bromine in 15 ml of carbon tetrachloride is added in 35 minutes at 0° C. to a solution of 35.4 g (0.08 mole) of 3,3'-dithiobis(2-trichloromethyloxazolidine) in 150 ml of carbon tetrachloride.

The above cold sulfenyl bromide is then added to a mixture of 22.1 g (0.15 mole) of phthalimide, 20.2 g (0.20 mole) of triethylamine) and 150 ml carbon tetrachloride over a period of 40 minutes at −5° to −10° C. The mixture is stirred at −5° to −10° C. for an additional 0.5 hour and then at ambient temperatures for 18 hours after which time it is filtered. The filter cake is washed with ether and the combined filtrates are freed of solvents to yield solids which are washed with ice water (4×500 ml) in a Waring Blendor and are then washed with absolute ethanol at ambient temperatures and dried to yield 34 g (62% conversion) of product, m.p. 162°-5° C. The structure as set forth below is consistent with the infrared spectrum and other analyses.

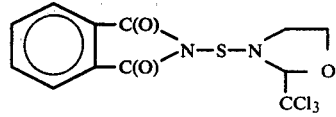

EXAMPLE 2

N-[(21-Trichloromethyloxazolidino)thio]succinimide

Into a solution of 66.5 g (0.15 mole) of 3,3'-dithiobis (2-trichloromethyloxazolidine) and 250 ml of carbon tetrachloride is passed 10.6 g (0.15 mole) of chlorine at a temperature of −10° C. over a period of 30 minutes. The solution is stirred an additional 15 minutes at −10° C.

The above sulfenyl chloride solution is then added in 35 minutes to a solution, maintained at −10° C., of 29.7 g (0.3 mole) of succinimide, 33.3 g (0.33 mole) of triethylamine and 450 ml of tetrahydrofuran. The mixture is stirred at 0° to −10° C. for one hour and then at ambient temperatures for two hours after which time it is added to 3 liters of water. The bottom, organic layer is separated and freed of solvents under reduced pressures. The wet solids are stirred with 0.5% aqueous sodium hydroxide at 0° C., filtered and then dried. Additional washing with isopropanol, followed by ether yields 64 g (69% conversion) of white solid product, m.p. 202°-4° C. The structure as set forth below is consistent with the infrared spectrum and other analyses.

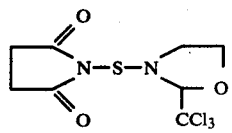

EXAMPLE 3

N-[(2-Trichloromethyloxazolidino)thio]maleimide

A cold solution of 0.2 mole (2-trichloromethyloxazolidino)sulfenyl chloride is added to a mixture of 19.4 g (0.2 mole) of maleimide, 22.2 g (0.22 mole) of triethylamine and 500 ml of tetrahydrofuran at a temperature of 0° C. over a period of 45 minutes. The mixture is stirred for an additional one hour at 0° to 5° C. and at ambient temperature for one hour, and then is added to three liters of water. The volatiles are removed under reduced pressures from the bottom phase of solids and liquid and the resulting residue is stirred with 500 ml of isopropanol. The mixture is filtered and the filter cake washed with a minimum of hexane to yield, after drying, 43 g (65% overall conversion based on the disulfide) of the desired product, a white solid, m.p. 161°-4° C. The infrared spectrum of the product is consistent with the structure as set forth below and other analyses.

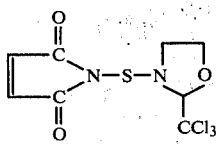

EXAMPLE 4

N-[(5-Phenyl-2-trichloromethyloxazolidino)thio]phthalimide

Into a solution of 59.5 g (0.1 mole) of 3,3'-dithiobis[(5-phenyl-2-trichloromethyl)oxazolidine] and 150 ml carbon tetrachloride is passed 7.2 g (0.1 mole) of chlorine over a period of 20 minutes at a temperature of −5° C. The solution is stirred an additional 10 minutes at −5° C.

The sulfenyl chloride solution is then added in 30 minutes to a mixture of 17.0 (0.2 mole) of potassium phthalimide and 450 ml of tetrahydrofuran at −5° C. After stirring at 0° to −5° C. for an additional 2.5 hours, the mixture is filtered and the volatiles are removed under reduced pressures. The residue is treated with toluene and the mixture is then filtered. The filtrate is then flash-evaporated, and the resulting semi-solid is treated with ethyl ether at 5° C. and filtered cold to yield 19 g (22% conversion) of white solid product, m.p. 152°-7° C. The structure of the product as set forth below is consistent with the infrared spectrum and other analyses.

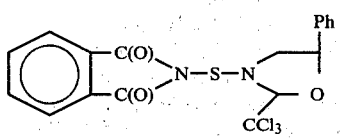

EXAMPLE 5

N-[(2-Phenyloxazolidino)thio]phthalimide

A mixture of 14.9 g (0.1 mole) of N-(2-hydroxyethyl)-benzylidenimine, 32.4 g (0.1 mole) of N,N'-thiobisphthalimide and 1.4 liters of methylene chloride is stirred at ambient temperatures for three days after which time the mixture is filtered. The filtrate is freed of solvents under reduced pressures. The residue is treated with ethyl ether, and the mixture is then refiltered. The ether is flash-evaporated, and the residue is then extracted with benzene. The benzene is removed under reduced pressures. The residue is washed with ether to yield 3.5 g (11% conversion) of cream-colored solid product, m.p. 125°-8° C. The structure of the product as set forth below is consistent with the infrared spectrum and other analyses.

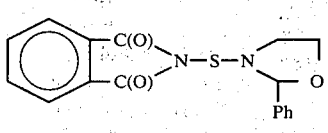

EXAMPLE 6

N-[(5-Phenyl-2-trichloromethyloxazolidino)thio]succinimide

Into a solution of 100 g (0.168 mole) of 3,3'-dithiobis[(5-phenyl-2-trichloromethyl)oxazolidine] and 150 ml of carbon tetrachloride is passed 11.9 g (0.168 mole) of chlorine at a temperature of −10° C. over a period of 15 minutes.

After stirring the above solution for an additional 15 minutes at −10° C., it is added over 30 minutes to a solution maintained at −10° C., of 33.3 g (0.336 mole) of succinimide, 37.3 g (0.373 mole) of triethylamine and 600 ml of tetrahydrofuran. The mixture is stirred an additional 75 minutes at −10° C. and two hours at ambient temperatures, and then is added to 3 liters of water. The mixture is extracted with 300 ml of methylene chloride after which time the volatiles are removed under reduced pressures. The residue is washed successively with 0.5% aqueous sodium hydroxide at 0° C., water isopropanol and ether to yield 88 g (66% conversion) of white solid product, m.p. 143°-6° C. The structure of the product as set forth below is consistent with the infrared spectrum and other analyses.

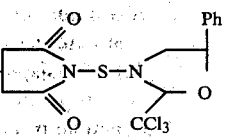

The corresponding compounds wherein the "R" group (in structural formula in Summary of Invention, supra.) is either 1,2-cyclohex-4-endiyl, 1,2-cyclohexanediyl, or 4-methyl-1,2-cyclohexanediyl are provided by the use of 1,2-cyclohex-4-endicarboxylic acid imide, 1,2-cyclohexanedicarboxylic acid imide or 4-methyl-1,2-cyclohexanedicarboxylic acid imide instead of the imides of Examples 1-6. These compounds likewise provide results comparable to the compounds of corresponding Examples 1-6, with respect to effectiveness as scorch-retardants with high bloom resistance.

EXAMPLE 6a

N,N'-Bis[(2-trichloro-methyloxazolidino)thio]pyromellitic Diimide

Into a solution containing 3,3'-dithiobis(2-trichloromethyloxazolidine) (0.125 mole) and methylene chloride (250 ml), is passed 8.9 g. (0.125 mole) of chlorine at a temperature of −10° C. over a period of 10 minutes. The solution is stirred an additional 15 minutes at −10° C.

The above sulfenyl chloride solution is then added over a period of 45 minutes to a mixture maintained at 15° C., of 21.6 g. (0.10 mole) of pyromellitic diimide, 28.3 g. (0.28 mole) of triethylamine and 600 ml of dimethylformamide. After stirring at ambient temperatures for three hours, the mixture is filtered, the filter cake is washed successively with 4×200 ml of ethyl ether, 4×800 ml of water in a waring Blendor, and is air-dried to yield 35 g. (35% conversion) of white solid product, m.p. 265° (sinters). The structure below, is consistent with the infrared spectrum and other analyses.

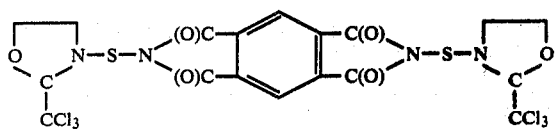

EXAMPLE 7

N-(Morpholinothio)phthalimide

The procedure of J. P. Lawrence, U.S. Pat. No. 3,838,114 (1974) is used to prepare the above compound, m.p. 208°–10° C. (lit. 210°–12° C.). The structure below is consistent with the infrared spectrum.

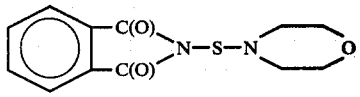

EXAMPLE 8

N-[Spiro(cyclohexane-1,2'-oxazolidino)thio]phthalimide

A solution of 7.2 g (0.045 mole) of bromine in 45 ml of carbon tetrachloride is added in 45 minutes to a solution at −5° C. of 17.2 g (0.05 mole) of bis[spiro(cyclohexane-1,2'-oxazolidino)] disulfide prepared from the amine, sulfur chloride and triethylamine in methylene chloride.

The clear, dark red solution is stirred an additional 10 minutes at −5° to −10° C., and is added to a mixture of 14.7 g (0.1 mole) of phthalimide, 13.1 g (0.13 mole) of triethylamine and 100 ml of carbon tetrachloride at −15° C. over a period of 30 minutes. After stirring additionally for 1.5 hours at −15° C. and for 18 hours at ambient temperatures, the mixture is filtered; the filtrate is flash-evaporated and the resulting residue is triturated with ethyl ether (3×30 ml) to yield 18 g (56% conversion) of a white solid product (m.p. 121°–4° C.) The structure below is consistent with the infrared spectrum.

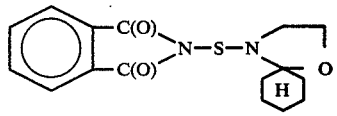

EXAMPLE 9

N-(Piperidinothio)phthalimide

The process of J. P. Lawrence, U.S. Pat. No. 3,838,114 (1976) is used to prepare the above compound (m.p. 181°–2° C.). The structure below is consistent with the infrared spectrum.

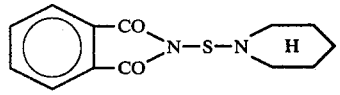

EXAMPLE 10

N-[N'-Benzyl-N'-ethylamino)thio]phthalimide

The above compound is prepared according to the procedure of J. P. Lawrence, *N-(Aminothio)-Imide Cure Modifiers*, Paper No. 36, ACS Rubber Division Meeting, New Orleans, LA. The melting point and infrared spectrum confirms the structure of the compound to be as shown below.

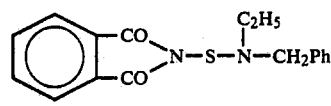

EXAMPLE 11

N-[Spiro(cyclohexane-1,2'-oxazolidino)thio]succinimide

Into a solution of 34.4 g (0.1 mole) of bis[spirocyclohexane-1,2'-oxazolidino)] disulfide and 150 ml carbon tetrachloride is passed 7.1 g (0.1 mole) of chlorine at a temperature of −10° C. over a period of 15 minutes. The solution is stirred an additional 15 minutes at −10° C.

The above sulfenyl chloride solution is then added in 15 minutes to a solution, maintained at −10° C. of 19.8 g (0.2 mole) of succinimide, 22.2 g (0.22 mole) of triethylamine and 500 ml of tetrahydrofuran. The mixture is stirred for an additional hour at −10° C., at ambient temperatures for two hours and then is added to 5 liters of water. The bottom organic phase is washed with 0.5% aqueous sodium hydroxide at 0° C., washed with distilled water, dried with magnesium sulfate, filtered and the filtrate is then freed of solvents to give a residue which is treated with ethyl ether. The mixture is filtered and the filtrate flash-evaporated to yield 35 g (65% conversion) of the desired product, an amber liquid contaminated with the oxazolidinodisulfide. The structure below is consistent with the infrared spectrum.

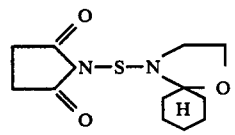

EXAMPLE 12

N-Phenyl-N-[(2-trichloromethyloxazolidino)thio]benzamide

A cold solution of 0.2 mole of (2-trichloromethyloxazolidino)sulfenyl chloride is added in 30 minutes to a solution of 39.5 g (0.2 mole) of benzanilide, 22.2 g (0.22 mole) of triethylamine and 400 ml of tetrahydrofuran maintained at −10° C. The mixture is stirred for an additional two hours at 0° to −10° C. and then for 18 hours at ambient temperatures after which time it is filtered and the filter cake washed with additional tetrahydrofuran. The combined filtrates are freed of volatiles at reduced pressures; the residue is taken up in methylene chloride, and then ethyl ether is added to precipitate a white solid which, after filtering and drying, yields 59 g (69% overall conversion based on the disulfide), of the desired product, (m.p. 158°–60° C.).

The structure below is consistent with the infrared spectrum and other analyses.

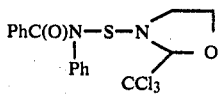

EXAMPLE 13

N,N'-Bis[(2-trichloromethyloxazolidino)thio]oxanilide

A cold solution of 0.3 mole of (2-trichloromethyloxazolidino) sulfenyl chloride is added over a period of 10 minutes to a mixture, maintained at −10° C., of 33.6 g (0.14 mole) of oxanilide, 33.3 g (0.33 mole) of triethylamine and 600 ml tetrahydrofuran. After stirring at −10° C. for one hour and at ambient temperatures for 20 hours, the mixture is filtered. The solids are treated with methylene chloride and the mixture is again filtered. The filtrate, after washing with water, is freed of volatiles under reduced pressures to give a residue which is then treated with ether. The resulting mixture is filtered to yield, after drying, 35 g (37% overall yield based on the disulfide) of the desired white solid product (m.p. 250°-3° C.). Its infrared spectrum is consistant with the structure shown below.

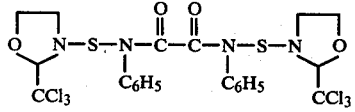

EXAMPLE 14

N,N'-Dimethyl-N,N'-bis[(2-trichloromethyloxazolidino)thio]oxamide

A solution of 53.6 g (0.52 mole) of sulfur dichloride is added to a mixture of 23.2 g (0.2 mole) of N,N'-dimethyloxamide and one liter of methylene chloride over a period of 10 minutes while at a temperature of 20° C. After stirring an additional five minutes, there is then added at 20° C. over a 15 minute period 44.4 g (0.4 mole) of triethylamine in an equal volume of methylene chloride. The mixture is stirred an additional 1.5 hours at ambient temperatures and then the volatiles are removed under reduced pressures. The residue is treated with benzene and the resulting mixture filtered. The filtrate, after flash-evaporating, yields 32 g of amber liquid (sulfenyl chloride).

To a solution of the above sulfenyl chloride in 1.2 liters of methylene chloride, is added a solution of 24.8 g (0.13 mole) of 2-trichloromethyloxazolidine, 14.1 g (0.14 mole) of triethylamine and 150 ml of methylene chloride over a period of 30 minutes while at a temperature of 0° C. After stirring an additional one hour at 0° C. and one hour at ambient temperatures, the mixture is filtered and the filtrate is flash-evaporated. The resulting residue is treated with ether, and then filtered. The filtrate is flash-evaporated to yield 39 g (35% overall conversion) of the desired product, an amber liquid. The infrared spectrum confirms the structure set forth below for the product.

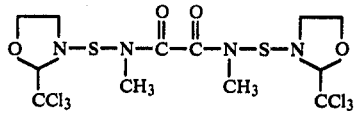

EXAMPLE 15

N-butyl-N[(2-trichloromethyloxazolidino)thio]acetamide

A solution of 45 g (0.238 mole) of 2-trichloromethyloxazolidine, 26.4 g (0.26 mole) of triethylamine and 200 ml of methylene chloride is added over a one hour period to a cold (0° C.) solution of 0.263 mole of N-butyl-N-chlorothioacetamide, prepared from N-butylacetamide, sulfur dichloride and triethylamine. After stirring for one hour at 0° to 5° C., the volatiles are removed under reduced pressures. The residue is treated with ether and then filtered. The filtrate is then flash-evaporated to yield 81 g (100% conversion) of product (an amber oil). The product is then purified by eluting with ethermethylene chloride from Fluorisil. The structure for the product as set forth below is in accordance with its infrared analysis and other analyses.

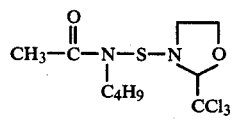

EXAMPLE 16

N-[(2-Trichloromethyloxazolidino)thio]diacetamide

A cold solution of 0.1 mole of (2-trichloromethyloxazolidino)-sulfenyl chloride is added over a period of 10 minutes to a solution at 0° C. of 10.1 g (0.1 mole) of diacetamide, 11.1 g (0.11 mole) of triethylamine and 600 ml of trichloroethylene. The mixture is stirred for an additional two hours at 0° to 5° C. and for one hour at ambient temperatures, and then the volatiles are removed under reduced pressures to give a semi-solid residue which is treated with ether. The mixture is filtered and the filtrate is then flash-evaporated. The residue is triturated with hexane and then washed with ether to yield 10 g (31% overall conversion based on the disulfide) of the desired white solid product (m.p. 83°-6° C.). The structure of the product as shown below is in accordance with its infrared spectrum and other analyses.

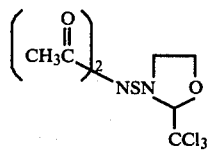

EXAMPLE 17

N-[(3-Phenyl-2-trichloromethylimidazolidino)thio]phthalimide

The method of preparation for the sulfenyl chloride from its precursor, 3,3'-dithiobis (3-phenyl-2-trichloromethyl)imidazolidine (prepared by azeotroping a toluene solution of N-phenylethylenediamine, chloral and acetic acid) has been described in previous examples.

To a solution of 14.7 g (0.1 mole) of phthalimide, 10.1 g (0.11 mole) of triethylamine and 500 ml of tetrahydrofuran at 0° C. is added a cold solution of 0.1 mole of the above sulfenyl chloride in 200 ml carbon tetrachloride over a period of 45 minutes. The mixture, after stirring for one hour at 0° C. and then two hours at ambient temperatures, is filtered to give a residue which is extracted with hexane. The hexane extracts are chilled to 0° C. and then filtered. The filtrate is freed of volatiles under reduced pressures. The resulting residue is extracted with ether to yield, after removing the solvent, 29 g (66% conversion) of the desired product (an amber viscous oil which solidifies on standing). The structure of the product as shown below is in accordance with its infrared spectrum and other analyses.

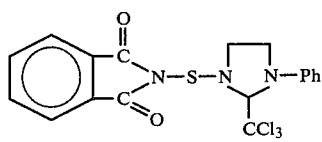

EXAMPLE 18

N,N-Bis[(2-trichloromethyloxazolidino)thio]acetamide

A solution of 0.1 mole of (2-trichloromethyloxazolidino)sulfenyl chloride is added to a solution of 5.9 g (0.1 mole) of acetamide, 11.1 g (0.11 mole) of triethylamine and one liter of tetrahydrofuran at a temperature of 0° C. over a period of 30 minutes. The mixtures, after stirring for one hour at 0° C. and then at ambient temperatures for one hour, are added to five liters of water. The bottom layer is separated, dried with magnesium sulfate, filtered and the volatiles removed under reduced pressures to give a turbid amber oil which is treated with a minimum of methylene chloride. The mixture is filtered and the solvent is removed from the filtrate under reduced pressures. The residue is extracted with hexane; and the hexane is then removed to yield 10 g (40% conversion) of product (a yellow viscous liquid). The structure of the product as shown below is in accordance with its infrared spectrum and other analyses.

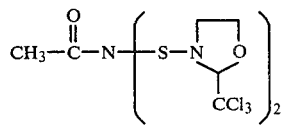

EXAMPLE 19

N,N'-Bis(cyclohexylthio)oxanilide

The above compound having the structure shown below is prepared by the method of Example I, U.S. Pat. No. 3,855,261, that issued Dec. 17, 1974.

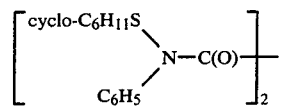

EXAMPLE 20

N,N'-Bis(cyclohexylthio)oxamide

The above compound having the structure as shown below is prepared by the method of Example II, U.S. Pat. No. 3,855,261, that issued Dec. 17, 1974.

EXAMPLE 21

N-[(2-Trichloromethylthiazolidino)thio]phthalimide

The compound, 3,3'-dithiobis (2-trichloromethylthiazolidine), is prepared by the addition over a period of 45 minutes of 17.5 g (0.13 mole) of sulfur chloride in 100 ml of ethyl ether to a solution of 54 g (0.26 mole) of 2-trichloromethylthiazolidine and 28.3 g (0.28 mole) of triethylamine in 450 ml ethyl ether at 10° C. After stirring for an additional 30 minutes at 10° C. and for three hours at ambient temperatures, the mixture is filtered and the volatiles are removed under reduced pressures to yield 47.5 g (77% conversion) of the amber liquid disulfide intermediate.

To 31 g (0.065 mole) of the above disulfide intermediate in 150 ml carbon tetrachloride is added over a period of 30 minutes a solution of 10.4 g (0.065 mole) of bromine in 30 ml carbon tetrachloride at 0° to −5° C. The solution is stirred an additional 30 minutes after which time it is added over a period of 30 minutes to a mixture of 22.2 g (0.12 mole) of potassium phthalimide and 200 ml ethyl ether at −2° to −10° C. After stirring additionally for three hours at 0° to −10° C. and then for three hours at ambient temperatures, the mixture is freed of volatiles under reduced pressures. The residue is taken up in methylene chloride, and the solution is washed with cold water (5×400 ml), dried with MgSO, filtered and then flash-evaporated to yield 26.5 g (57% conversion) of semi-solid product. The structure shown below is consistent with the infrared spectrum and other analyses of the product.

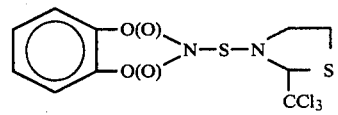

| Recipe 1, EPDM (For Evaluations in Tables I and IV) | |
|---|---|
|  | Parts by Weight |
| EPDM Rubber | 100 |
| Carbon Black (FEF) | 100 |
| Process oil | 65 |
| ZnO | 5 |
| Stearic Acid | 2 |
| Sulfur | 2 |
| MBT (Mercaptobenzothiazol) | 1.5 |
| Pennac NB Ultra (Accelerator) | 2.0 |
| Retarder | 0.5 |

The scorch (tms+3) for the EPDM Recipe 1 is measured at 270° F. The conventional 30-minute cure at 320° F. is used for the bloom observation at least one week after curing. The data is converted to percentage of the non-blooming control containing no retarder. The commercial EPDM accelerator, Pennac NB Ultra, is a very fast, non-blooming accelerator of the dithiocarbamate type. One of the candidate retarders is used also at two other levels (0.75 and 1.00 phr.). The 30-minute cure at 320° F. is also used for heat aging (7 days at 250° F.) studies measuring the Shore A Hardness and the Tensile Strength before and after the oven aging. Table IV shows that the tensile and hardness changes of the cures containing a retarder are practically the same as the changes of the cure without retarder.

Recipe 2

| Natural Rubber (For Evaluation in Table II) | |
|---|---|
| | Parts by Weight |
| Natural Rubber (SMR-5) | 100 |
| Carbon Black (HAF) | 50 |
| Process Oil | 5 |
| ZnO | 5 |
| Stearic Acid | 2 |
| Sulfur | 3 |
| Accelerator | (see below) |
| Retarder | 0.5 |

The accelerator for the Natural Rubber Recipe 2 is either 0.75 phr of N-cyclohexyl-2-benzothiazylsulfenamide (Pennac CBS), or a combination of 1.00 phr of 2,2'-di(benzothiazyl) disulfide (Pennac MBTS) with 0.3 phr of N,N'-diphenylquanidine (Pennac DPG), or a combination of 0.75 phr of Pennac CBS with 0.3 phr of tetramethylthiuram disulfide (Methyl Thiram). In all three cases the scorch (tms+3) is measured at 250° F., and the conventional 20 minute cure at 302° F. is used for bloom observation at least one week after the cure. Two of the candidate retarders are also used at other levels (0.75 and 1.00 phr.).

Recipe 3

| Neoprene | |
|---|---|
| | Parts by Weight |
| Neoprene W | 100 |
| Maglite D | 4 |
| SRF Black | 60 |
| Circolite Oil | 12 |
| ZnO | 5 |
| Amine Antioxidant | 1 |
| N,N'-Diethylthiourea | 0.75 |
| Retarder | 1.00 |

Using the test Recipe 3, the retarders of Examples 1, 2, and 3 yield a Mooney scorch (tms +3) retardation (at 250° F.) of 140–180% of the control which did not contain any retarder, and are thus deemed to be excellent retarders. The amine antioxidant used is octylated diphenylamine (Pennox ODP).

Recipe 4

| SBR (For Evaluation in Table V) | |
|---|---|
| | Parts by Weight |
| SBR 1502 | 100.0 |
| HAF Black | 50.0 |
| Circolite Oil | 5.0 |
| ZnO | 5.0 |
| Stearic Acid | 2.0 |
| Sulfur | 3.0 |
| MBTS | 1.5 |
| DPG | 0.3 |

Recipe 4-continued

| SBR (For Evaluation in Table V) | |
|---|---|
| | Parts by Weight |
| Retarder | 0.5 |

The scorch (tms +3) is measured at 270° F. and the bloom observation is made on the 30-minute cure [302° F.] at least one week after the cure.

The retarder evaluation results of selected compounds at Examples 1–21 in Recipe No. 1 (EPDM) are given in Table I, below.

Table I

| Retarder Activity in EPDM (Recipe 1) | | |
|---|---|---|
| Compound of Example No. | Bloom (a) | Scorch, % of control |
| Control | NB | 100 |
| PVI | BL | 125 |
| 1 | NB | 150 |
| 2 | NB | 146 |
| 2(b) | NB | 159 |
| 2(c) | NB | 161 |
| 3 | NB | 150 |
| 4 | NB | 125 |
| 5 | NB | 125 |
| 6 | NB | 150 |
| 6a | NB | 121 |
| 7 | BL | 100 |
| 8 | NB | 100 |
| 9 | BL | 100 |
| 10 | BL | 100 |
| 11 | NB | 100 |
| 12 | BL | 175 |
| 13 | BL | 120 |
| 14 | NB | 80 |
| 15 | NB | 100 |
| 16 | NB | 100 |
| 17 | NB | 86 |
| 18 | NB | 98 |
| 19 | BL | 150 |
| 20 | NB | 126 |
| 21 | BL | 93 |

(a)NB-no bloom observed Bl-bloom observed
(b)0.75 phr was used instead of 0.5 phr
(c)1.00 phr was used instead of 0.5 phr The retarder evaluation results of the compounds evaluated in Recipe 2 are given in Table II, below.

Table II

| Retarder Activity in Natural Rubber (Recipe 2; 0.75 phr. Pennac CBS) | | |
|---|---|---|
| Compound of Example No. | Bloom (a) | Scorch, % of Control |
| Control | NB | 100 |
| PVI | BL | 275 |
| 1 | NB | 150 |
| 1(b) | NB | 156 |
| 2 | NB | 172 |
| 2(c) | NB | 150 |
| 2(c,d) | NB | 175 |
| 2(c,e) | NB | 225 |
| 2(b) | NB | 189 |
| 3(b) | NB | 189 |
| 3(c) | NB | 150 |
| 3(c,d) | NB | 150 |
| 3(c,e) | NB | 175 |
| 4 | NB | 158 |
| 5 | NB | 175 |
| 6 | NB | 167 |
| 6a(b) | NB | 136 |
| 7 | BL | 200 |
| 9 | BL | 200 |
| 10 | BL | 192 |
| 11 | NB | 83 |
| 12 | BL | 156 |
| 13 | BL | 168 |

Table II-continued

Retarder Activity in Natural Rubber
(Recipe 2; 0.75 phr. Pennac CBS)

| Compound of Example No. | Bloom (a) | Scorch, % of Control |
|---|---|---|
| 19 | BL | 272 |

(a)NB-no bloom observed BL-bloom observed
(b)Pennac CBS (0.75 phr) and Methyl Thiram (0.3 phr) are used instead of Pennac CBS
(c)Pennac MBTS (1.0 phr) and Pennac DPG (0.3 phr) are used instead of Pennac CBS
(d)0.75 phr is used instead of 0.5 phr of the retarder
(e)1.0 phr is used instead of 0.5 phr of the retarder Thermal Stability data for a number of the retarder candidates is presented in Table III.

Table III

| Days at 50° | Thermal Stability Melting Point, °C. For Compound of Example | | | |
|---|---|---|---|---|
| | 1 | 2 | 3 | 7 |
| 0 | 173-5 | 201-5 | 167-170 | 206-209 |
| 0.25 | 173-5 | 201-5 | 168-171 | 188-201 |
| 1 | 172-5 | 200-203 | 168-170 | 180-198 |
| 8 | 172-4 | 200-203 | 168-171 | 185-201 |
| 20 | 172-5 | 200-203 | 168-171 | 183-199 |

The effect of the retarders of Examples 2 and 3 on the aging of the cures is shown in Table IV.

Table IV

EPDM-Recipe 1, Heat Aging (of 30 min.-cures), 7 days at 250° F.

| Compound of Example No. | Use Level phr | Scorch % of Control | Bloom (1) | Tensile, psi Prior to Aging | Tensile, psi After Aging | % Change | Hardness Shore A Prior to Aging | Hardness Shore A After Aging |
|---|---|---|---|---|---|---|---|---|
| Control | None | 100 | NB | 2230 | 2240 | +0.4 | 71 | 77 |
| 2 | 0.5 | 164 | NB | 2170 | 2230 | +2.8 | 72 | 77 |
| 2 | 0.75 | 159 | NB | 2080 | 2230 | +6.7 | 72 | 78 |
| 2 | 1.00 | 161 | NB | 2060 | 2260 | +9.7 | 71 | 77 |
| 3 | 1.00 | 168 | NB | 2130 | 2210 | +3.7 | 73 | 78 |
| PVI | 0.5 | 112 | BL | 2220 | 2250 | +1.3 | 71 | 76 |

(1) NB-no bloom observed BL-bloom observed

The retarder evaluation results of selected compounds of Examples 1-21 in Recipe 4 (SBR) are given in Table V, below:

Table V

Retarder Activity in SBR (Recipe 4)

| Compound of Example No. | Bloom (a) | Scorch, %(d) of Control |
|---|---|---|
| Control | NB | 100 |
| PVI | BL | 120 |
| 2 | NB | 120 |
| 2(b) | NB | 130 |
| 2(c) | NB | 140 |
| 3 | NB | 125 |
| 3(c) | NB | 130 |
| 17 | NB | 106 |
| 18 | NB | 106 |
| 20 | NB | 159 |
| 21 | NB | 101 |

(a)NB-no bloom observed, BL-bloom observed
(b)0.75 phr instead of 0.5 phr retarder
(c)1.0 phr instead of 0.5 phr retarder
(d)The scorch (tms +3) is measured As demonstrated by the melting points (Table III) of the three imides N-[(2-trichloromethyloxazolidino)thio]phthalimide (Example 1), N-[(2-trichloromethyloxazolidino)thio] succinimide (Example 2), and N-[(2-trichloromethyloxazolidino)thio]maleimide (Example 3), the selected group of oxazolidinothioimides is significantly more thermally stable than the N-(morpholinothio) imide of Example 7 which is derived from a cyclic amine containing a ring-oxygen, i.e., a 6-membered rather than a 5-membered cyclic amine.

The differences in thermal stability however, cannot be made solely responsible for the high degree of scorch retardation of the retarders of this invention. The three oxazolidinothioimides of Examples 1, 2, and 3 and the morpholinothioimide of Example 7 differ in thermal stability but each are active scorch retarders in natural rubber, with the least stable (compound of Example 7) being the most active. In EPDM, however, the least stable compound (Example 7) (together with the compounds of Examples 9 and 10) is the least active (not active). The compound N-[(N'-Benzyl-N'-ethylamino)-thio]phthalimide (Example 10) is claimed to be one of the best retarders of the aminothioimides as pointed out in Rubber Chemistry and Technology, Vol. 49, p. 333 (1976). The amine of N-(piperidinothio)phthalimide (Example 9) is more basic than that of N-(morpholinothio)phthalimide (Example 7), but these two imides are equally active retarders in natural rubber (and EPDM). Pyrrolidine and piperidine are equally basic (Rubber Chemistry and Technology, 46, p. 76) but the imide N-(Piperidinothio)phthalimide (Example 9) of the latter is a scorch retarder while that of the former is useless (not tested because of its thermal instability). Thus a generalization in the activity-stability relationship cannot be made. It is difficult to arrive at a generalization with respect to retardation activity in various elastomer types.

According to U.S. Pat. No. 3,910,864, the retarder N-(morpholinothio)succinimide does not exhibit the desirable double action of retarding the scorch and retaining the original properties of the vulcanizate upon aging. The corresponding N-[(2-trichloromethyloxazolidino)thio]succinimide (Example 2) as well as the maleimide derivative N-[(2-trichloromethyloxazolidino)thio]maleimide (Example 3), representing the selected group of imides, however, are not only good scorch retarders but also are not detrimental to the retention of the original properties upon vulcanizate aging (Table IV).

The selectivity of the cxazolidinothioimides retarders of this invention and their uniqueness as scorch retarders is further evidenced by the following:

(a) The phthalimides N-[(2-trichloromethyloxoazolidino)thio]phthalimide (Example 1), N-[(5-Phenyl-2-trichloromethyloxazolidino)thio]phthalimide (Example 4), and N-[(2-phenyloxazolidino)thio]phthalimide (Example 5) and the succinimides N-[(2-trichloromethyloxazolidino)thio]succinimide (Example 2) and N-[(5-Phenyl-2-trichloromethyloxazolidino)thio]succinimide (Example 6), having a phenyl-or trichloromethyl-substituent in 2-position and phenyl or no substituent in the 5-position of the oxazolidine ring, are active and non-blooming retarders. The phthalimide N-[spiro(cyclohexane-1,2'-oxazolidino)thio]phthalimide (Example 8) and the succinimide N-[spiro(cyclohexane-1,2'-oxazolidino)thio]succinimide (Example 11), derived from 2-pentamethylene-oxazolidine do not exhibit the expected scorch retardation. To the contrary, N-[spiro(cyclohexane-1,2'-oxazolidino)thio]succinimide (Example 11) caused additional scorchiness in natural rubber. Thus the retarders are limited to the aminothioimides derived from the amines 2-trichloromethyl-, 2-phenyl-, and 2-trichloromethyl-5-phenyloxazolidine, with 0-2 substituents in the phenyl.

(b) Surprisingly, the acetamide derivatives N-butyl-N[(2-trichloromethyloxazolidino)thio]acetamide (Example 15) and N,N-bis[(2-trichloromethyloxazolidino)thio]acetamide (Example 18), the diacetimide N-[(2-trichloromethyloxaolidino)thio]diacetimide (Example 16) and the oxalamide-derivative N,N'-dimethyl-N,N'-bis[(2-trichloromethyhloxazolidino)thio]oxamide (Example 14) of 2-trichloromethyloxazolidine do not show the retardation activity expected according to U.S. Pat. Nos. 3,910,864 and 4,006,140, while the oxalamide N,N'bis[(2-trichloromethyloxazolidino)thio]oxanilide (Example 13) is an active retarder but produces bloom. Thus, the retarders are limited to imides and cannot include amides; furthermore the limitation is to imides of phthalic tetrahydrophthalic, hexahydrophthalic, bicyclo[2.2.1]heptane-2,3-dicarboxylic, 7-oxabicyclo[2.2.1]heptane-2,3-dicarboxylic, bicyclo[2.2.1]hept-5-ene-2,3-dicarboxylic and 7-oxabicyclo[2.2.1]hept-5-ene-2,3-dicarboxylic, pyromellitic, maleic, and succinic acids.

(c) The lack of retardation activity in EPDM and the blooming in natural rubber produced by N-(morpholinothio)phthalimide (Example 7) and N-(piperidinothio)phthalimide (Example 9) limit the ring structure of the amine to a 5-membered ring containing another heteroatom in addition to the nitrogen. Thus, it would appear that the amine moiety could be an oxazolidine, thiazolidine and imidazolidine, but (d) the surprising lack of scorch retardation activity (of at least 10% over the control) of the 2-trichloromethylthiazolidinoimide of Example 21 and of the 3-phenyl-2-trichloromethylimidazolidinoimide of Example 17 excludes the thiazolidine and imidazolidine amine-moieties. As analogues of oxazolidine, however, they are expected to be active retarders.

What is claimed:

1. A N-(oxazolidinothio)imide compound having the structural formula:

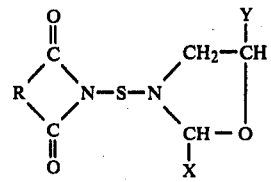

wherein R is an organic divalent radical selected from the group consisting of ortho-phenylene, 1,2-cyclohex-4-enediyl, 1,2-cyclohexanediyl, 4-methyl-1,2-cyclohexanediyl, 1,2-ethanediyl, and 1,2-ethenediyl; furthermore R can be the divalent radical:

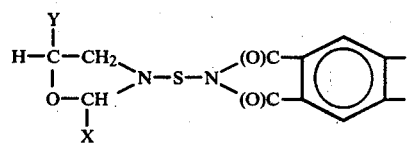

X is a monovalent organic radical selected from the group consisting of phenyl and trichloromethyl radicals; Y is hydrogen with the proviso that Y can be phenyl when X is trichloromethyl.

2. The compound as defined in claim 1 wherein R is orthophenylene, X is trichloro-methyl, and Y is hydrogen.

3. The compound as defined in claim 1 wherein R is a 1,2-ethanediyl radical, X is trichloromethyl, and Y is hydrogen.

4. The compound as defined in claim 1 wherein R is a 1,2-ethenediyl radical, X is trichloromethyl, and Y is hydrogen.

5. The compound as defined in claim 1 wherein R is ortho-phenylene, X is trichloromethyl, and Y is phenyl.

6. The compound as defined in claim 1 wherein R is ortho-phenylene, X is phenyl, and Y is hydrogen.

7. The compound as defined in claim 1 wherein R is a 1,2-ethanediyl radical, X is trichloromethyl, and Y is phenyl.

* * * * *